United States Patent [19]

Cowing

[11] Patent Number: 5,442,948
[45] Date of Patent: Aug. 22, 1995

[54] APPARATUS AND METHOD FOR DETERMINING AMOUNT OF GASES DISSOLVED IN LIQUIDS

[75] Inventor: Scott Cowing, Gaithersburg, Md.

[73] Assignee: The United States of American as represented by the Secretary of the Navy, Washington, D.C.

[21] Appl. No.: 677,941

[22] Filed: Apr. 1, 1991

[51] Int. Cl.⁶ .................................................. G01N 7/00
[52] U.S. Cl. ................................................. 73/19.05
[58] Field of Search ............... 73/19.05, 61 R; 55/270

[56] References Cited

U.S. PATENT DOCUMENTS

| | | | |
|---|---|---|---|
| 2,138,141 | 11/1938 | Cromer et al. | 73/151 |
| 2,680,060 | 6/1954 | Natelson | 23/253 |
| 3,171,722 | 3/1965 | Natelson | 23/253 |
| 3,791,104 | 2/1974 | Clithesoe | 55/86 |
| 4,315,890 | 2/1982 | Tamers | 422/58 |
| 4,607,342 | 8/1986 | Seiden et al. | 364/558 |
| 4,700,561 | 10/1987 | Dougherty | 73/19.05 |
| 4,745,794 | 5/1988 | Steichen et al. | 73/19 |
| 4,844,843 | 7/1989 | Rajendien | 261/30 |
| 4,862,729 | 9/1989 | Toda et al. | 73/19.05 |
| 4,924,695 | 5/1990 | Kolpak | 73/61.1 R |

FOREIGN PATENT DOCUMENTS 2190196 11/1987 United Kingdom .

*Primary Examiner*—Sandra L. O'Shea
*Assistant Examiner*—Raymond Y. Mah
*Attorney, Agent, or Firm*—Howard Kaiser

[57] ABSTRACT

The quantity of gases dissolved in liquids is determined by introducing a liquid sample into a hollow cylinder with a plunger, retracting the plunger to create a void space into which gases originally dissolved in the liquid sample diffuse, compressing the gases into a reduced volume, measuring the absolute pressure of the gases, and calculating the amount of gases originally dissolved in the liquid from the absolute pressure, the temperature, the vapor pressure of the liquid at the prevailing temperature, the volumes of liquid and the final volume of the gas, by using the ideal gas law.

4 Claims, 1 Drawing Sheet

APPARATUS AND METHOD FOR DETERMINING AMOUNT OF GASES DISSOLVED IN LIQUIDS

The invention described herein may be manufactured and used by or for the Government of the United States for governmental purposes without the payment of any royalties thereon or therefor.

BACKGROUND OF THE INVENTION

This invention is related to apparatus and a method for determining the amount of gases, such as oxygen, nitrogen, carbon dioxide and carbon monoxide, dissolved in liquids such as water or samples of blood. More specifically, it relates to apparatus which, unlike most conventional apparatus used for such determinations, does not employ liquid mercury, which is toxic and represents a health hazard. When mercury spills occur in workplaces such as laboratories, mercury vapor creates an inhalation hazard at room temperature because of the low concentrations of mercury vapor required to cause ill effects.

DESCRIPTION OF THE PRIOR ART

A variety of apparatus for determining the amount of gases dissolved or entrapped in liquids is known to the art.

A device referred to as the Van Slyke apparatus for determining the amount of gases dissolved in liquids has been commercially available for many years. It employs a sample chamber, a shutoff valve, a mercury manometer and a mercury reservoir acting as a sealing fluid and as a means of producing vacuum.

U.S. Pat. No. 2,138,141 describes apparatus for determining the amount of gas contained in drilling must used in drilling oil and gas wells. It employs a sample cylinder with a shutoff valve and piston and a Bourdon-type of pressure gauge protected by a metal diaphragm.

U.S. Pat. No. 2,680,060 describes a device embodying the features of the Van Slyke apparatus referred to above employing mercury as a sealing fluid and further employing a cylinder with a plunger to adjust the level of the mercury in the apparatus.

U.S. Pat. No. 3,171,722 describes a device resembling that of U.S. Pat. No. 2,680,060 above used for injecting a gas sample into a gas chromatograph.

U.S. Pat. No. 4,315,890 relates to a sample tube for liquids having volatile components dissolved therein, and also having a reagent supported on an inert support such as glass wool in a portion of the sample tube, for indicating qualitatively by change in color whether certain volatile components, such as ethanol, are present in the sample liquid.

U.S. Pat. No. 4,607,342 describes a device for determining the quantity of carbon dioxide dissolved in carbonated beverages comprising a computer which controls solenoid-operated valves for admitting a sample of the beverage into a test chamber, stirring it to release carbon dioxide, measuring the pressure in the chamber, and automatically computing therefrom the level of carbonation of the beverage.

U.S. Pat. No. 4,745,794 describes functionally similar apparatus for determining the level of carbonation of beverages.

British patent 2,190,196 describes apparatus for determining the quantity of gases dissolved in liquids comprising a conical flask having a side neck for a movable piston and a center neck for a pressure transducer.

SUMMARY OF THE INVENTION

It is the object of the present invention to provide apparatus for determining the quantity of gases dissolved in liquids which is more economical than apparatus now known, and which does not require the use of mercury which is a potential health and safety hazards in laboratories. It is a further object to provide a method of determining the quantity of gases dissolved in liquids which is convenient and which can be carried out by individuals with modest skills in chemical laboratory procedures.

The apparatus of the present invention comprises a hollow cylinder with a plunger slidably disposed therein and a pressure transducer. The method of the present invention involves introduction of a liquid sample into the cylinder, the positioning of the plunger in three predetermined positions, and taking a pressure reading, from which the quantity of dissolved gases may be calculated.

DESCRIPTION OF THE PREFERRED EMBODIMENT OF THE INVENTION

Figure 1:
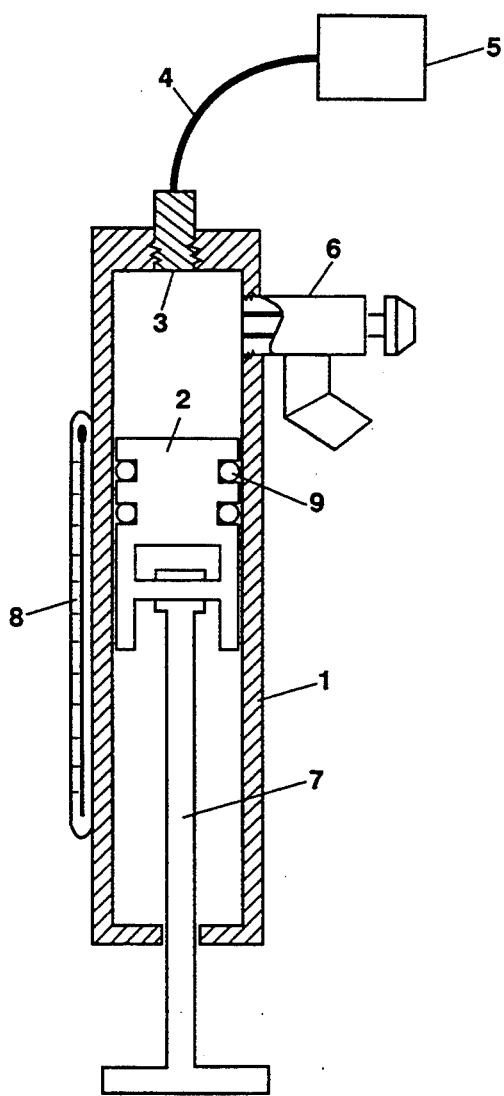
FIG. 1 is a cross-section of the preferred embodiment of this invention.

With reference to FIG. 1, into an elongated hollow cylinder 1 having an open end and a closed end is provided with a snugly fitting cylindrical plunger 2 capable of sliding back and forth in the cylinder in an axial direction. The plunger forms a gas-tight and liquid-tight seal along its periphery and the inside surface of the cylinder.

Figure 2:
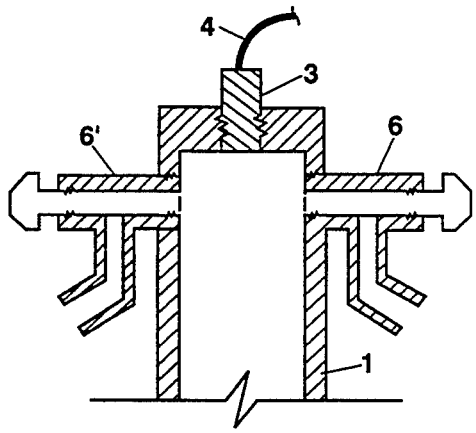
FIG. 2 is a modification of the embodiment.

Near the closed end of the cylinder there is provided a tight-shutoff valve 6, which is connected to the cylinder and whose purpose is to admit liquid into the cylinder and to expel gas and liquid therefrom. Optionally, as illustrated in FIG. 2, two such shutoff valves 6 and 6' may be provided, one for admitting liquid into the cylinder, and the other one for draining such liquid or for expelling gas.

Also provided near the closed end of the cylinder is a pressure transducer 3, whose output is transmitted to a pressure indicator 5. Preferably, the pressure transducer comprises four strain gauges securely fastened to a metal diaphragm and exposed to the interior of the cylinder (not shown). The strain gauges are connected by electrical wiring 4 to the pressure indicator 5. The four strain gauges, connected in a Wheatstone bridge circuit (not illustrated), have electrical resistances which vary in response to variations in pressure exerted upon the metal diaphragm by the gas pressure in the cylinder. A supply voltage is provided across the input terminals of the Wheatstone bridge. Across the output terminals of the Wheatstone bridge, there will appear a voltage signal which is directly related to the absolute pressure of the gas in the cylinder. This output voltage is amplified as needed and displayed by a voltmeter, which may be calibrated in units of absolute pressure. The pressure transducer as described, or its equivalent, is well known in the art. A pressure transducer of the type having a metal diaphragm with strain gauges produces a negligible volume displacement as the metal diaphragm flexes in response to changes in pressure. The volume of the cylinder, which must be accurately known for accurate determinations of the amounts of dissolved gases, thus is virtually unaffected by the pressure inside the cyclinder.

Figure 3:
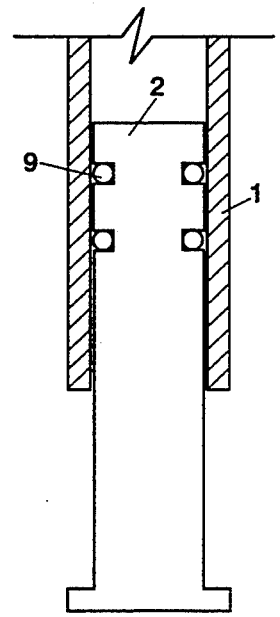
FIG. 3 illustrate a modification of the plunger.

To the plunger 2, there may be attached a handle 7, as shown in FIG. 1, to facilitate moving the plunger back and forth in the cylinder bore. Alternatively, the plunger may be a solid cylindrical body which can be manipulated without a separate handle, as shown in FIG. 3. Calibrated volume markings may be provided on the stem of the plunger or on the handle as appropriate.

Gas-tightness and liquid-tightness around the periphery of the plunger in the cylinder may be assured by O-rings 9 fitted into circumferential grooves in the peripheral surface of the plunger, with the O-rings slidably bearing against the smooth inside wall of the cylinder.

A thermometer 8, such as a mercury-in-glass thermometer, may be strapped to the outside of the cylinder to indicate the temperature of the cylinder. Alternatively, the junction of a thermocouple (not illustrated) may be attached to the outside of the cylinder, with electrical wires connected to a potentiometer whose voltage reading is directly related to the temperature of the cylinder.

The cylinder and plunger preferably are made of steel, stainless steel, brass, aluminum, or glass.

The method of determining the quantity of gases dissolved in a liquid is described as follows:

(1) Initially, the cylinder is set up with the closed end up and the plunger end down. A predetermined volume of sample liquid is introduced into the cylinder by first expelling the air from the cylinder through the open shutoff valve by displacement of the plunger toward the closed end; then drawings an excess of liquid into the cylinder by dipping the outlet of the open shutoff valve into the liquid and pulling the plunger away from the closed end of the cylinder; and finally expelling excess liquid and entrapped gas or air bubbles by moving the plunger to a predetermined point inscribed on the plunger handle, and closing the shutoff valve. The sample volume, typically, is 10 ml.

Alternatively, when two valves are employed as illustrated in FIG. 2, both valves are opened simultaneously to allow sample liquid to flow through the volume in the cylinder, the sample liquid being pumped by external means. After all air has been expelled from the cyclinder volume, both valves are closed.

(2) Retracting the plunger so as to create a volume much larger than that of the liquid, whereby a void volume under vacuum is created above the liquid and into which gases originally dissolved in the liquid sample diffuse. Typically, the void volume thus created should be from five to ten times the volume of the liquid sample to insure virtually complete diffusion of the dissolved gases into the void volume. Also diffusing into the void volume will be vapors of the constituents of the liquid, such as water, each constituent of the liquid attaining a partial pressure commensurate with its vapor pressure, its concentration in the liquid and its activity coefficient.

(3) The apparatus is now turned into a horizontal position to allow the sample liquid to spread out and expose a large surface to maximize the rate of diffusion of dissolved gases into the void volume. The plunger is held in its position until the pressure indicator gives a constant reading, indicating that the gases originally dissolved in the liquid have disengaged therefrom and reached equilibrium within the expanded volume.

(4) The cylinder is returned to its original position and the plunger is moved toward the closed end of the cylinder so as to compress the gases, the volume of the cylinder being less than that in steps (2) and (3) but greater than the volume of the liquid. The cylinder volume, typically, is 12 ml, the gas volume 2 ml, and the liquid volume 10 ml.

(5) The absolute pressure is read on the pressure indicator. The quantity of gases dissolved in the liquid is now calculated from the ideal gas law:

$$n = (P - P_v) V_{gas}/(RTV_{liq}), \text{ where}$$

$n$ = gram-moles of gas dissolved per ml of liquid
$P$ = pressure reading in cylinder, atm.
$P_v$ = vapor pressure of liquid constituents, atm., at sample temperature
$V_{gas}$ = gas volume in cylinder, typically 2 ml
$R$ = universal gas constant, 82.06 atm-ml/gram-moles/deg K.
$T$ = absolute temperature, deg K., or deg C. + 273
$V_{liq}$ = liquid volume, typically 10 ml Other modifications of this invention will be apparent to those skilled in the art, all falling within the scope of the invention as described here and claimed in the following.

What is claimed is:

1. A method of determining the amount of gases dissolved in liquids with cylindrical apparatus comprising:
   (a) introducing a predetermined first volume of liquid into a cylinder in a vertical position said cylinder having an open end, a closed end, a slidable plunger capable of moving back and forth within said cylinder and a shutoff valve, by displacing the plunger with said shutoff valve open, and expelling all nondissolved gases said cylinder being provided with a pressure transducer connected to a pressure indicator;
   (b) expanding the volume in the cylinder by retracting the plunger to a first predetermined position in the cylinder creating a second volume greater than that of the liquid, with the shutoff valve closed;
   (c) moving the cylinder from a vertical to a horizontal position to increase the exposed surface area of the liquid;
   (d) allowing gases dissolved in the liquid to diffuse therefrom and to reach equilibrium within the expanded volume in the cylinder;
   (e) compressing the gases in the cylinder by moving the plunger to a second predetermined position within the cylinder creating a third volume less than that in step (b) but greater than that of the liquid; and
   (f) determining the absolute pressure in the cylinder displayed by said indicator, whereby the amount of gases dissolved in the liquid may be calculated from the absolute pressure and the predetermined first volume and third volume.

2. A method of determining the amount of gases dissolved in liquids in accordance with claim 1 in which the first volume is from 5 to 50 milliliters and the volume of the gas in step (e) is from 0.5 to 5 ml.

3. A method of determining the amount of gases dissolved in liquids with cylindrical apparatus comprising:

(a) providing a cylinder having a closed end, an open end, a slidable plunger capable of movement back and forth within said cylinder, a shutoff valve and a pressure measuring means;

(b) placing the cylinder in a vertical position with the closed end up and the open end down;

(c) expelling air from the cylinder through the said valve by displacement of the plunger from the open end toward the closed end of the cylinder;

(d) providing liquid to the open shutoff valve and drawing an excess of the liquid into the cylinder by moving the plunger away from the closed end of the cylinder;

(e) expelling entrapped undissolved gas and excess liquid from the cylinder by moving the plunger to a predetermined first position within the cylinder creating a first volume of liquid and closing the valve;

(f) retracting the plunger to a second predetermined position in the cylinder creating an expanded second volume greater than the said first volume;

(g) moving the cylinder from a vertical position to a horizontal position to increase the exposed surface area of the liquid;

(h) allowing the gases dissolved in the liquid to diffuse therefrom and to reach equilibrium within the expanded second volume in the cylinder;

(i) compressing the gases in the cylinder by moving the plunger to a third predetermined position within the cylinder creating a third volume less than the second volume but greater than the said first volume; and (j) determining the absolute pressure of the gases in the cylinder, whereby the amount of gases dissolved in the liquid may be calculated from the absolute pressure and the first volume and third volume.

4. A method of determining the amount of gases dissolved in liquids with cylindrical apparatus comprising:

(a) providing a cylinder having a closed end, an open end, a slidable plunger capable of movement back and forth within said cylinder, two shutoff valves and a pressure measuring means;

(b) opening both said shutoff valves with the plunger in a first predetermined position;

(c) pumping liquid into one of said valves thereby expelling substantially all undissolved gas from the cylinder through the other said valve;

(d) closing both valves whereby a first volume of liquid is captured in the cylinder;

(e) retracting the plunger to a second predetermined position in the cylinder creating an expanded second volume greater than the said first volume;

(f) ensuring that the cylinder is in a horizontal position to increase the exposed surface area of the liquid;

(g) allowing the bases dissolved in the liquid to diffuse therefrom and to reach equilibrium within the expanded second volume in the cylinder;

(h) compressing the bases in the cylinder by moving the plunger to a third predetermined position within the cylinder creating a third volume less than the said second volume but greater than the said first volume; and (i) determining the absolute pressure of the bases in the cylinder, whereby the amount of gases dissolved in the liquid may be calculated from the absolute pressure and the first volume and third volume.

* * * * *

UNITED STATES PATENT AND TRADEMARK OFFICE
CERTIFICATE OF CORRECTION

PATENT NO.    : 5,442,948  
DATED         : August 22, 1995  
INVENTOR(S)   : Scott Gowing Page 1 of 1

It is certified that error appears in the above-identified patent and that said Letters Patent is hereby corrected as shown below:

<u>Title page,</u>
Item [75], Inventor should read -- Scott Gowing --.
Item [73], Assignee should read -- The United States of America as represented by the Secretary of the Navy, Washington, D.C. --.

Signed and Sealed this

Twenty-first Day of January, 2003

JAMES E. ROGAN
*Director of the United States Patent and Trademark Office*